(12) United States Patent
Iversen et al.

(10) Patent No.: US 6,423,099 B1
(45) Date of Patent: Jul. 23, 2002

(54) SAFETY CLUTCH FOR A PROSTHETIC GRIP

(75) Inventors: Edwin K. Iversen, Salt Lake City; James R. Linder, West Jordan; Steven R. Kunz, Salt Lake City; Arthur D. Dyck, Draper; Harold H. Sears, Salt Lake City, all of UT (US)

(73) Assignee: Motion Control, Inc., Salt Lake City, UT (US)

( * ) Notice: Subject to any disclaimer, the term of this patent is extended or adjusted under 35 U.S.C. 154(b) by 0 days.

(21) Appl. No.: 09/576,398

(22) Filed: May 22, 2000

(51) Int. Cl.[7] .............................. A61F 2/54; A61F 2/68; B66C 1/00
(52) U.S. Cl. .......................................... 623/64; 294/106
(58) Field of Search .............................. 623/64, 57, 63; 901/14, 31, 27, 15, 5, 8; 294/106, 111, 115

(56) References Cited

U.S. PATENT DOCUMENTS

| | | | | |
|---|---|---|---|---|
| 4,094,016 A | * | 6/1978 | Eroyan | 623/65 |
| 4,114,464 A | * | 9/1978 | Schubert et al. | 74/89.14 |
| 4,246,661 A | * | 1/1981 | Pinson | 623/64 |
| 4,623,354 A | * | 11/1986 | Childress et al. | 623/25 |
| 4,923,477 A | | 5/1990 | Horvath | |
| 5,046,996 A | | 9/1991 | Horvath | |
| 5,108,140 A | * | 4/1992 | Bartholet | 294/106 |
| 5,280,981 A | * | 1/1994 | Schulz | 194/106 |
| 5,378,033 A | * | 1/1995 | Guo et al. | 294/116 |
| 5,762,390 A | * | 6/1998 | Gosselin et al. | 294/106 |
| 5,800,571 A | * | 9/1998 | Carlson et al. | 623/57 |
| 6,244,644 B1 | * | 6/2001 | Lovchik et al. | 294/111 |

* cited by examiner

Primary Examiner—Corrine McDermott
Assistant Examiner—Alvin Stewart
(74) Attorney, Agent, or Firm—Thorpe North & Western, LLP

(57) ABSTRACT

A grip device for an artificial or prosthetic arm, including at least two opposable digits and a drive linkage powered by a drive motor. When the drive motor is powered it enables the two opposable digits to grip. The drive linkage includes a drive and transmission attached to the drive motor. A backlock is connected to the drive and transmission. Surrounding the backlock is a backlock housing which contains the drive, selected transmission elements, and a backlock. A stop element is also included for holding the backlock housing fixed with respect to ground. The stop element can be released to allow the backlock housing to move freely and to avoid power transmission without disrupting the operating structure of the transmission.

21 Claims, 5 Drawing Sheets

SAFETY CLUTCH FOR A PROSTHETIC GRIP

TECHNICAL FIELD

The present invention relates generally to a clutch mechanism used in a mechanical grip device, particularly useful as a prosthetic hand. More particularly, the present invention relates to a mechanical grip which is electrically driven and a safety clutch mechanism used to release the mechanical grip.

BACKGROUND

There are an estimated 100,000 individuals with the loss of arms or hands in the United States alone and as many as 10,000 new amputees each year. Research has been carried out in the area of providing prosthetic limbs for many years. The result of this research has provided complex multiple degrees-of-freedom hands, which are too large and complex to be feasible in the marketplace. In contrast, a number of more commercially viable and affordable one-degree-of-freedom hands have been created. These prosthetic hands are combined with powered prosthetic elbows. The hands and elbows are driven by small electric motors. Command signals to drive the powered motors are provided by electrodes which receive electrical signals from the amputee's remaining muscles.

The practical one-degree-of-freedom hands or grips that have become commercially available have a number of shortfalls. One of these problems is the weight of the hands. Prosthetic hands on the market, which have a relatively high gripping force, weigh over 16 ounces. For hands weighing less than 13 ounces, the strength of the grip is cut in half.

Another significant problem with these hands is the safety features that are incorporated into the hands. It is difficult to incorporate safety features because of the desire to have hands with lower cost and complexity. For each safety feature that is incorporated into the hand, the weight of the hand may increase.

One specific problem is providing a hand or grip that can release in an embarrassing or dangerous situation. For example, suppose an amputee is getting off a public transit bus. To exit the bus, the amputee must "grip" the provided handrail. When the amputee steps away from the bus, the hand must then release its grip. It is possible that the hand may fail to release from the handrail because of a power failure or some other problem. In that situation, there must be a way to release the hand or it could endanger the amputee. If the hand does not release, the amputee could be pulled by the bus. Alternatively, the prosthetic hand, elbow and their assemblies might be disengaged from the amputee and taken with the bus as it drives away. Notwithstanding the danger, it can be very aggravating to lose the arm because it is difficult to retrieve and such prosthetic devices are very expensive. Other situations can also be imagined which would also present danger or embarrassment to the amputee if the hand does not release, such as descending stairs, riding an escalator, climbing a ladder, or getting stuck on a shopping cart in a public place.

It is desirable to provide a system to allow an amputee to quickly and safely release the prosthetic hand. Safety release devices have been developed, but most are not easy to operate or do not release the hand in a dangerous situation. For example, a prosthetic hand or grip manufactured by Otto Bock of Duderstadt, Germany, can only be released if 40 pounds of pressure is applied against the fingers and thumb of its prosthetic device. The Otto Bock Greifer, a work terminal device, also has a release mechanism which unmeshes interlocking gears near the load on the gripping surfaces. A lever moves the shaft of a transmission gear and separates the driving gear from a gear on the load side. This allows gears near the load to spin freely and release the gripping surfaces.

One major disadvantage with a mechanism that actually disengages the gears is that the delicate balance between the gears is disrupted. When the gears are re-engaged 0t.here is a certain amount of movement that must take place to force the gears together. This re-engagement of the gears produces wear and tear on the gears. As the gears wear, they do not operate as efficiently and their operation noise increases. A second major disadvantage to the release mechanism for disengaging the gears is that it is not easily accessible in an emergency because the fingers of the hand must physically be pulled apart, which is difficult for a one-armed or no-armed person.

SUMMARY OF THE INVENTION

It has been recognized that it would be advantageous to develop a system to allow an amputee to quickly and safely, manually release a prosthetic hand with one motion. Specifically, the safety release should be easily accessible to the amputee in case of an emergency. When the safety release is engaged, the fingers move freely with very little force required to move them.

In accordance with one aspect of the present invention, a grip device includes at least two opposable digits and a drive linkage powered by a drive motor. When the drive motor is powered, it enables the two opposable digits to grip. The drive linkage includes a drive and transmission attached to the drive motor. A backlock is connected in-line to the drive and transmission. Surrounding the backlock is a backlock housing which contains selected transmission elements. The safety release mechanism includes the backlock housing, a stop member for holding the backlock housing fixed with respect to ground, and other links. The stop member can be released to allow the backlock housing to move freely without disrupting the operating structure of the transmission.

In accordance with another aspect of the present invention, the system includes a backlock housing, containing the drive, transmission, and backlock, and including a plurality of locking holes formed into the backlock housing. A spring loaded pin is releasably coupled into at least one locking hole in the backlock housing. When the pin is released, the backlock housing can move freely and the opposable digits of the system can be opened with relatively little force. Alternately, a friction break can be used to fix the backlock housing in place.

Additional features and advantages of the invention will be set forth in the detailed description which follows, taken in conjunction with the accompanying drawings, which together illustrate by way of example, the features of the invention.

DETAILED DESCRIPTION

Figure 1:
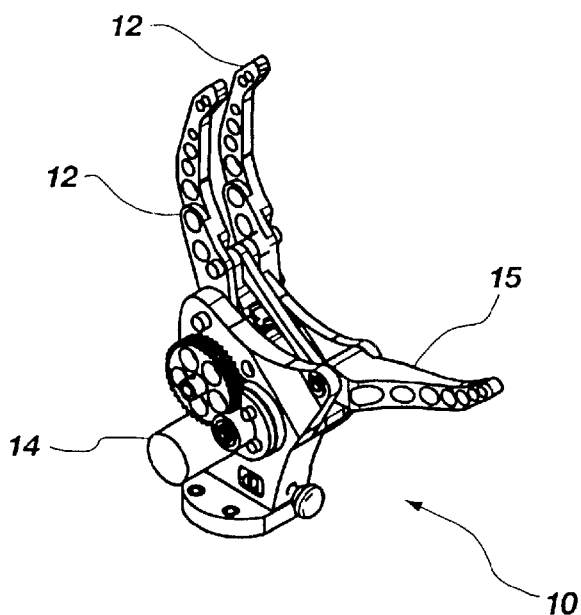
FIG. 1 is a perspective view of a preferred embodiment of a mechanical gripping hand.

For the purposes of promoting an understanding of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Figure 2:
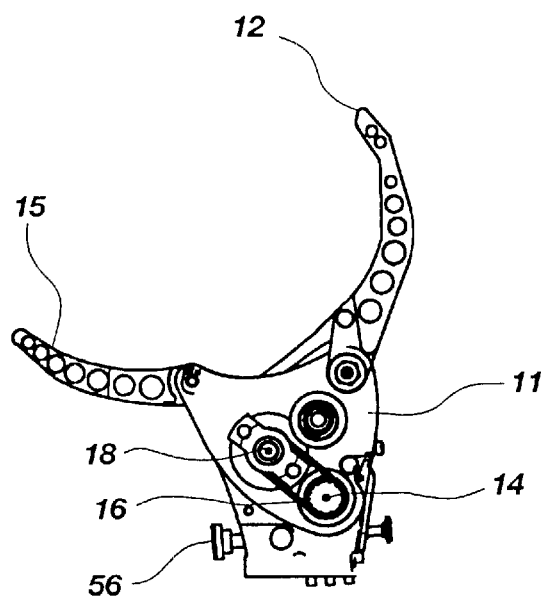
FIG. 2 is a side view of a preferred embodiment of the mechanical gripping hand as in FIG. 1.

As illustrated in FIGS. 1 and 2, a mechanical gripping system 10 is shown for use as a prosthetic hand and for grasping objects. A grip device includes at least two opposable digits 12 and 15 and a drive linkage inside the grip mechanism. The grip is powered by a drive motor 14 mounted into the grip base 11, and the drive motor enables the two opposable digits 12, 15 to grip. The motor can be a basket wound high torque to inertia motor with heavy duty graphite/copper composite brushes or another conventional heavy duty motor known to those skilled in the art.

Figure 3:
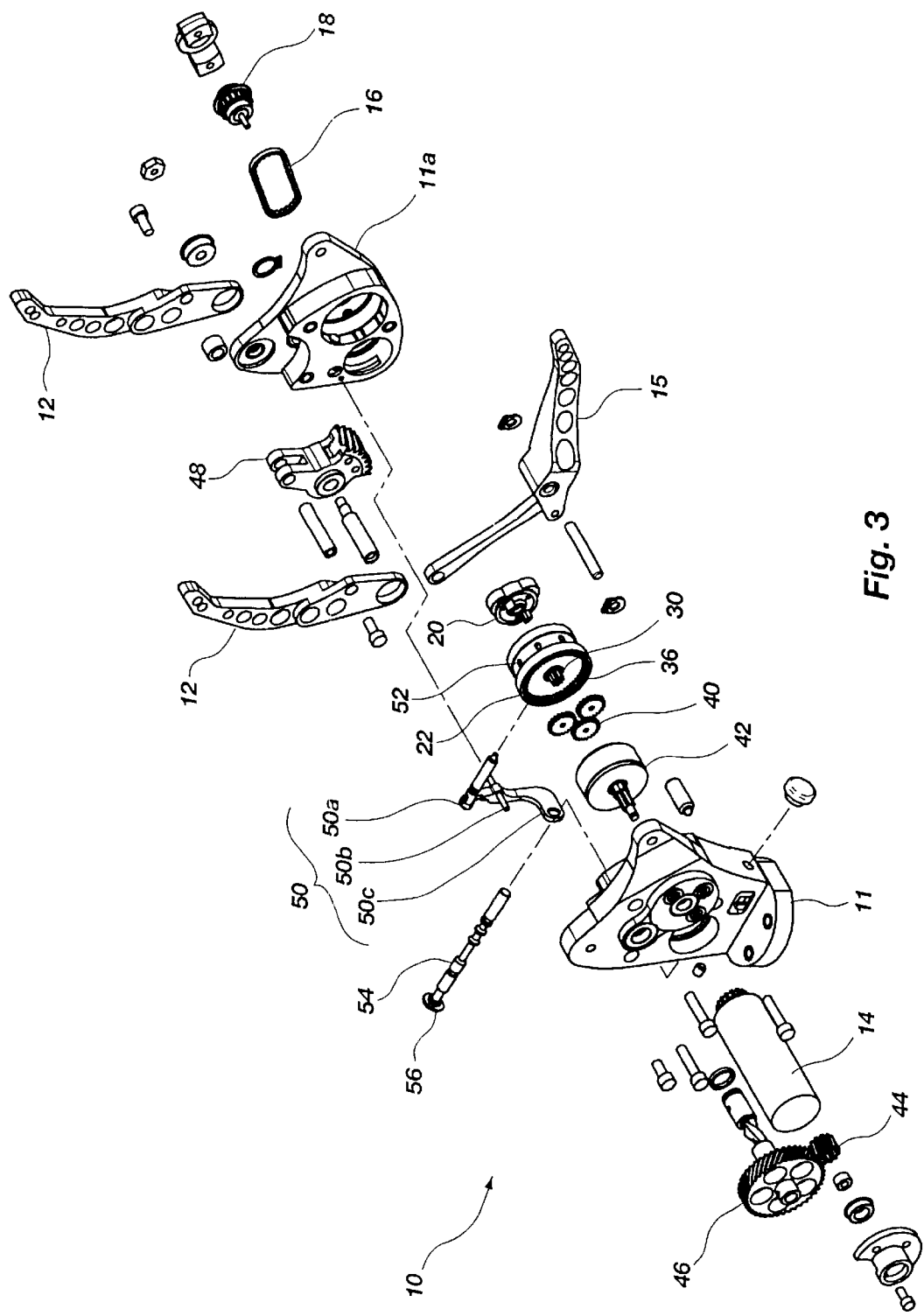
FIG. 3 is an exploded view of a mechanical gripping hand as in FIGS. 1 and 2.

Referring now to the exploded view of the mechanical gripping system as illustrated in FIG. 3, the drive linkage comprises a drive and transmission attached to the drive motor 14. More particularly, the drive includes a number of gear reductions and drive gears to transfer power for use in the opposing digits 12 and 15. The motor drives a belt 16 which in turn drives a friction planetary input 18.

The friction planetary input 18 drives three planetary friction rollers 20. The friction planetary rollers are contained within the backlock housing 22. In one embodiment, the friction planetary reduction includes a 0.0566 inch input shaft for the sun drive, 0.312 rollers for the planets and a 0.681 inch ring surrounding the sun drive and planetary friction rollers. This results in a speed reduction of 11.5:1. This friction planetary gear reduction also reduces the noise associated with high speed gears because of the compact nature and smooth surfaces of this type of reduction.

Figure 4:
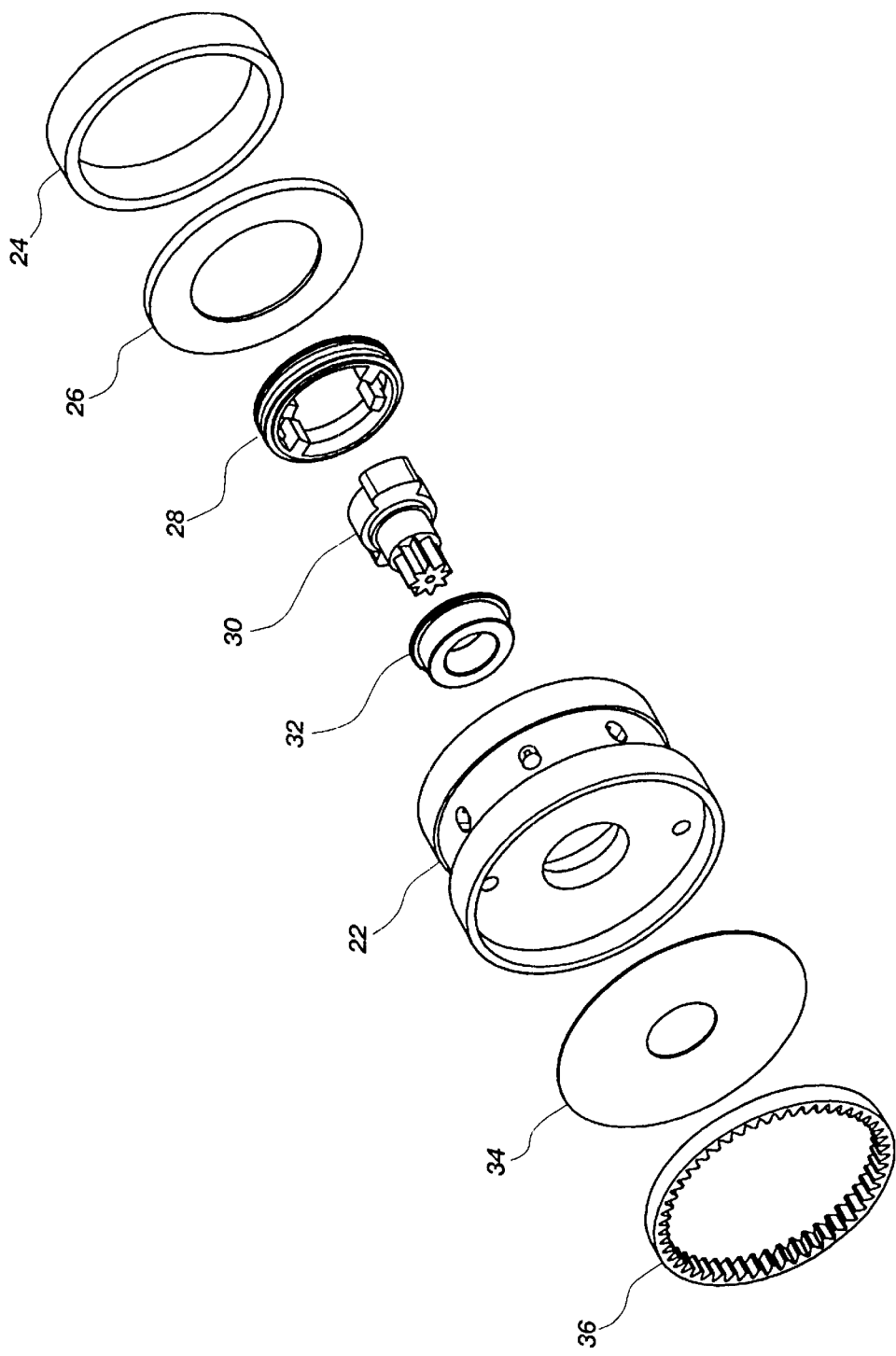
FIG. 4 is an exploded view of elements contained within a backlock housing as in FIG. 3.

FIG. 4 depicts an exploded view of the transmission elements that are contained within the backlock housing 22. The friction planetary input 18 drives the friction planetary rollers 20 through the stationary friction planetary ring 24 (FIGS. 3 and 4). The friction planetary ring is housed within the backlock housing. The friction planetary input is often known as a friction sun gear because it is the center shaft of the friction gear reduction. The friction sun gear causes the three or more planet rollers to rotate as one unit and then drive the backlock output. The backlock is a spring loaded assembly which can be driven in a clockwise or counterclockwise direction from the motor or power supply side of the transmission. Conversely, the backlock cannot be driven from the load or digit side.

The backlock is an important part of the hand's drive linkage. When an object is grasped, power cannot be cut to the hand motor without the backlock. A backlock allows the grip to be maintained without power being applied to the motor. This means that the opposable digits remain locked unless they are being driven by the motor. The backlock works by means of a spring inside a bore that uncoils and locks the backlock when it is back driven. If the backlock is driven in either direction from the friction planetary side, the spring coils and remains unlocked. Backlocks are well known to those skilled in the art and more than one configuration of backlock can be used.

Power is then transferred through the backlock output 30 which is surrounded by a bearing 32. All of these elements just discussed are contained in a first side of the backlock housing 22. An output washer 34 is mounted in a second side of the backlock housing and a geared planetary ring 36 is inserted over the output washer 34. An essential point to understand is that when the backlock housing is fixed in position or grounded relative to the rest of the mechanical gripping system then it cannot be back driven by the load from the opposing digits.

Returning now to FIG. 3, the planet gears 40 are contained within the geared planetary ring 36 and are driven by the backlock output 30. The backlock output is the sun gear for the planetary gears. The planet gears are driven by the sun shaft so that they roll around the geared planetary ring which produces a gear reduction ratio determined by the pitch diameter of the sun gear to the ring. The sun gear of the geared planetary is connected in-line to the two-speed transmission for high speed operations. The planet gears then drive the two-speed transmission cup 42 to provide greater torque at lower rotational speed than the sun gear. The two-speed transmission shifts the drive between the high speed sun gear and the high torque cup. A two-speed transmission allows the hand to have high speed while free running, and strength while grasping an object. The automatic two-speed transmission operates by means of a torque sensing spring which allows the transmission to change gear reductions when the transmission is loaded. A two-speed transmission allows the hand to be both strong and fast.

When the backlock housing is fixed, the low-speed gear reduction is the ratio of reduction from the sun gear to the ring gear. In the preferred embodiment of the invention, the reduction ratio of the sun gear to the ring gear can be 10:1. When the backlock housing is not fixed in position, then the ring gear is no longer grounded, which does not allow the transmission of torque.

The two-speed transmission 42 drives the pinion gear 44 or output gear, which then mates with and drives the 42-tooth gear, which is attached to the shaft of the three-tooth assembly 46. The three toothed gear drives the sector gear 48 which is attached to one set of the opposable digits 12 or fingers of the hand.

As mentioned, the backlock housing 22 contains selected elements of the transmission. This can include the friction planetary gears, backlock, and the toothed planetary gears. To provide the reduction effect of these gears, the backlock housing must be fixed. When the backlock is fixed, the transmission cannot be back driven. The only way the prior art was able to overcome this problem was by completely disengaging two of the gears (e.g. the pinion gear from the two-speed transmission) or by putting a very large amount of pressure on the digits to release a slip clutch. This method of disengaging the gears upsets the delicate balance of the clockwork-like transmission mechanism. The pressure method has the serious drawback that the fingers may not release if the amputee cannot apply enough pressure to the fingers.

In the preferred embodiment of the mechanical gripping system or prosthetic hand, a significantly improved method for releasing the grip has been developed. The backlock housing 22 includes a stop member for holding or fixing the backlock housing with respect to ground. In other words, the backlock housing is held in one position with respect to the rest of the mechanical gripping system or prosthetic hand (i.e. grounded). Then the stop member can be released to allow the backlock housing to move freely without disrupting the operating structure of the transmission. This is significant because no gears are disengaged.

The preferred stop member is a backlock housing with a plurality of stop holes 52 formed into the circumference of the backlock housing. A safety release assembly 50 is used to stop the movement of the backlock housing. A spring-loaded safety release pin 50a in the safety release assembly drops down into the stop holes and fixes the backlock housing relative to ground. The safety release pin 50a is spring-loaded so if it does not land directly on stop hole when it is inserted, the spring-loaded pin will be forced by a spring (not shown) down into the stop holes. The safety release assembly is mounted with a fulcrum pin 50b or levered release so the safety release arm 50c can be depressed to remove the safety release pin. The safety release arm is manually depressed by the amputee when there is an emergency and a need to release the grip. When the safety release pin is removed from the backlock housing, then it is able to spin freely and the gear reduction ratios provided by the friction planetary gear and the toothed planetary gear are bypassed.

After the backlock housing has been released, no torque can be transmitted in either direction through the transmission. This is due to the ungrounding of the friction planetary, backlock, and geared planetary. The gears all remain in contact with one another, but can spin relative to each other, thus allowing no power transmission. Only a small amount of gear friction has to be overcome to moves the fingers passively. Thus, only a few pounds of pressure (e.g. 1–4 pounds of pressure) is needed to open the digits after the safety mechanism is released. When the backlock housing is grounded, more than 40 pounds of pressure is required to open the digits.

In one embodiment of this device, the safety release assembly 50 is attached to the on/off shuttle switch 54. Conventionally, this switch controls the power to the mechanical gripping system or prosthetic hand and more specifically the motor 14. When the safety release assembly is connected to the on/off shuttle switch, this allows the amputee to simultaneously shut off the power to the hand and also release the safety release pin 50a from the backlock housing by pressing a single switch button 56. The use of a single button combining the two functions eliminates confusion possible with a two button-configuration.

Another configuration separates the on/off shuttle switch from the safety release assembly. This way the safety release arm 50c is separated from the on/off switch. Separating these functions is not necessarily as convenient, but it does allow a different colored or larger button to be used with the safety release assembly. In addition, an amputee may not want the power and safety functions directly linked.

The present system has the major advantage that it allows parts of the transmission to move freely after they have been released. This is especially valuable where certain gear reduction elements of the transmission can be released without disengaging any elements of the transmission. The gear ratio reduction amount which is removed from the system by releasing the backlock housing varies depending on which gear reduction elements are connected to the backlock housing. If a lower amount of gear reduction is desired to be removed from the system, only one set of planetary gears can be tied to the backlock housing. Conversely, if an increased amount of gear reduction is desired to be tied to the safety release, additional gearing components can be coupled to the backlock housing. For example, additional levels of gear reduction can be introduced or the two-speed transmission 42 can also be connected to the backlock housing.

Other methods of stopping of the backlock housing 22 or grounding it relative to the hand can be used. A second configuration for grounding the backlock in place is the use of a friction break on the end of the safety release assembly 50. This includes a drum or disk type break that can be released to free the backlock housing. Another configuration has one or more protrusions on the backlock housing and a holding pin as part of the safety release assembly against which the protrusions will be stopped. The backlock housing is then freed when the holding pin is moved. Another variation of this is forming flat areas on the backlock housing and using a rotatable pin with a rounded protrusion on one side to stop the rotation of the backlock housing. For example, if the backlock housing is octagon shaped, then the rounded side of the pin can be used to hold an edge of the polygon in place. When the pin is rotated and a flat side of the pin is presented, there is nothing to hold the backlock in place and it spins freely.

Referring again to FIG. 3, the finger 12 and thumb 15 are made of aluminum. They can also be made of a plastic which is a composite material made of long glass fibers and nylon. This plastic material has a high tensile strength and high notched impact strength. It is important for an amputee to have fingers and fingertips designed to augment prehension or grasping of a number of objects including keys, books, coffee cups, and utensils.

Figure 5A:
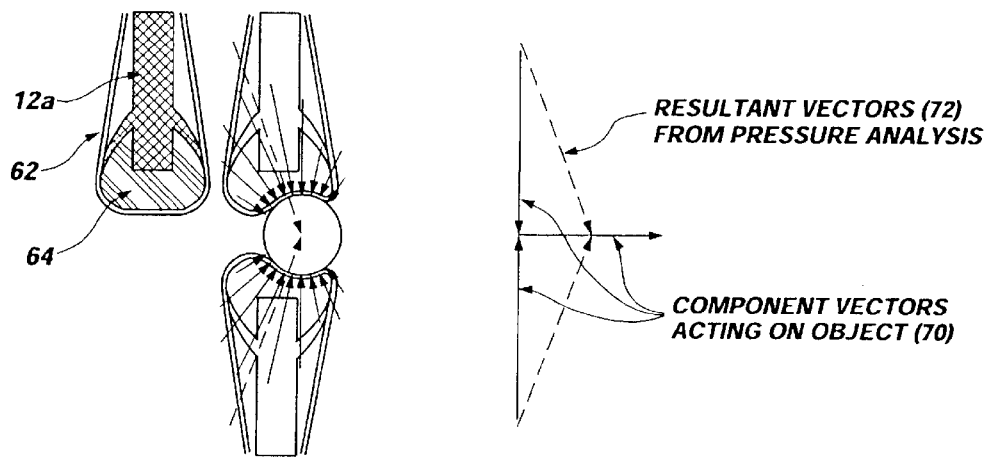
FIG. 5a illustrates conventional compliant fingertips and force vectors acting on an object grasped with such material.

Referring now to FIG. 5a, conventional compliant fingertips 12a (e.g. plastics) have certain component force vectors 70 that create resultant vectors 72, which tend to force an object being grasped from between the fingertips. Specifically, the fingertips are surrounded by a cosmetic glove or protective glove 62 and have a compliant material 64 adhered to the end of the fingertip.

Figure 5B:
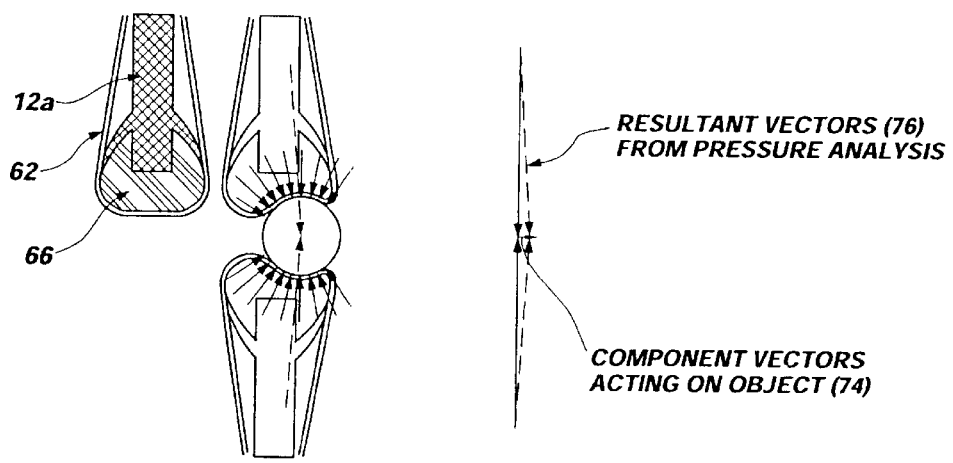
FIG. 5b illustrates hydrostatic fingertips and the force acting on an object grasped with hydrostatic material.

The prosthetic fingers 12a of this device use hydrostatic fingertips, as illustrated in FIG. 5b, which act like the natural fingertip and can significantly aid prehension. Encapsulated gel-like fingertips surrounded by a glove 62 allow pressures to build up within the fingertip. This creates equal normal pressures at the interface between the fingertip and the grasped object. Objects such as pencils, which are difficult to pick up with a prosthetic hand can easily be grasped with hydrostatic gel type fingertips. The hydrostatic fingertips are installed in a cavity 66, which is formed within the composite plastic molded fingertips. The component force vectors 74 for the hydrostatic fingertips produce significantly smaller resultant vectors 76. These reduced vectors help keep the object between the fingertips instead of forcing an object out. The hydrostatic material may be gel, oil, or other fluid.

Another significant disadvantage of conventional mechanical grips or prosthetic hands is that the length of the hand (such as the Otto Bock hand) does not allow a wrist to be incorporated while maintaining a hand length equal to that of a real adult hand. The internal structure of the prosthetic hand must be shortened by about 0.75 inches to integrate a wrist into the hand and still maintain a hand length equal to that of an actual adult hand.

Motors in prior art prosthetic hands have had a radial axis in-line with the radial axis of a human arm. When the motor used to power the prosthetic hand has a radial axis in-line with the radial axis of the arm, the hand structure cannot be shortened significantly. The present device rotates the radial axis of the motor so it is normal or 90 degrees to the radial axis of the amputee's arm axis. As described earlier, the motor drives a belt 16 which in turn drives a friction planetary input 18 (FIGS. 2 and 3). The belt or pulley drive is used for two reasons. First, the belt allows the motor to be placed in a transverse position, which contributes to the length reduction of the hand. The shortening of the drive mechanism in the hand allows a wrist member and drive to fit within the space of a normal human hand. Second, this belt/pulley system is more quiet than a gear drive.

Figure 6:
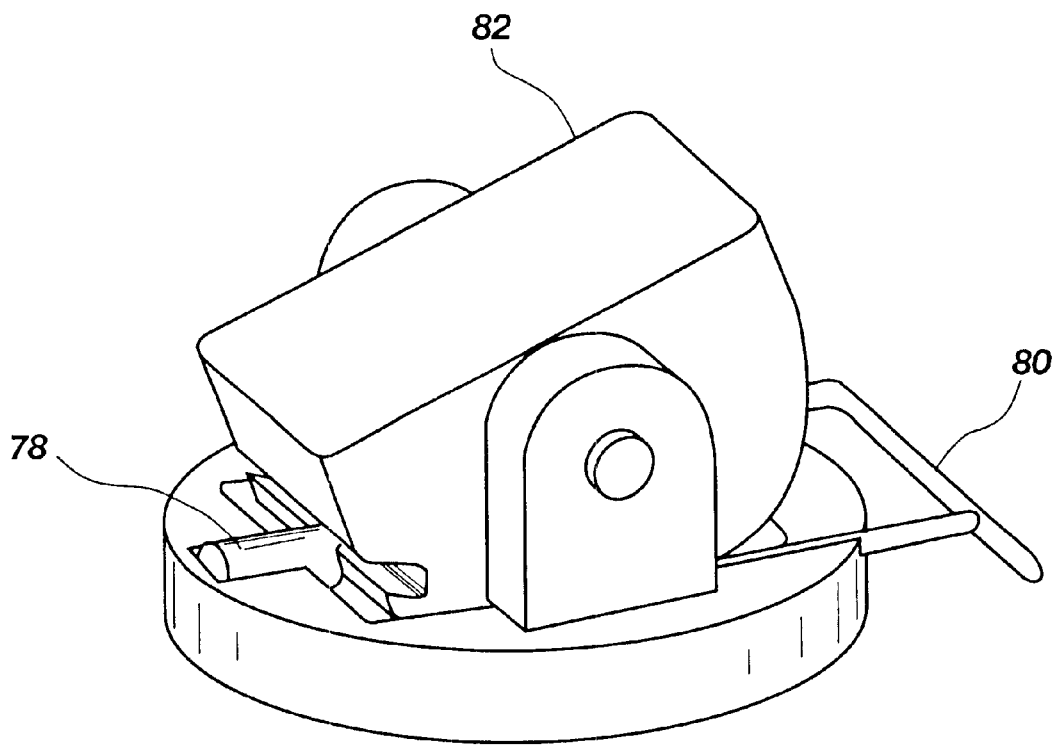
FIG. 6 illustrates a prosthetic hand mounted on a rotatable surface.

This significant rearrangement of the motor by using a belt/pulley system, as opposed to a direct gear drive, allows the machinery driving the grip device or prosthetic hand to be shortened. This in turn enables a mechanical wrist flexion or wrist rotation device to be attached to the prosthetic hand. As illustrated in FIG. 6, the prosthetic hand is mounted onto a rotatable surface 82 and a convenient lock allows the amputee to unlock, move, and re-lock the wrist. The wrist is unlocked by pushing the sliding latch 80 and locked by releasing the latch after the wrist has been repositioned. A spring 78 aids in moving and repositioning the latch.

A microprocessor controller is also included in the hand for several functions which are listed below.

A) The controller includes automatic adjustment of control parameters to the amputee's EMG signals and uses these signals to control proportionally the speed and grip force of the hand.

B) The controller limits the force of the prosthesis.

C) The power to the hand is shut off when the hand is inactive.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A grip device having at least two opposable digits and a drive linkage, powered by a drive motor, configured to enable the two opposable digits to grip, the drive linkage comprising:
   (a) a drive and transmission attached to the drive motor;
   (b) a backlock connected to the drive and transmission;
   (c) a backlock housing, coupled to the drive, transmission, and backlock; and
   (d) a stop means for holding the backlock housing with respect to ground, wherein the stop means can be released to allow the backlock housing to move freely without disrupting the operating structure of the transmission.

2. A grip device in accordance with claim 1, further comprising at least one locking hole in the backlock housing, wherein the stop means further comprises a spring loaded pin, releasably coupled into at least one locking hole in the backlock housing.

3. A grip device in accordance with claim 1, wherein the stop means further comprises a friction break.

4. A grip device in accordance with claim 1, wherein the stop means further comprises a protrusion on the backlock housing and a holding pin against which the protrusion will be stopped, wherein the backlock housing is freed when the holding pin is moved.

5. A grip device in a prosthetic arm having at least two opposable digits and a drive linkage configured to enable the two opposable digits to grip, the drive linkage comprising:
   (a) a drive motor mounted into the grip device;
   (b) a drive and transmission attached to the drive motor;
   (c) a backlock connected to the drive and transmission;
   (d) a backlock housing, containing the drive, transmission, and backlock, having a plurality of locking holes formed into the housing; and
   (e) a spring-loaded pin, configured to be releasably coupled into at least one locking hole in the backlock housing.

6. A grip device in accordance with claim 5, further comprising a pin release fastened to the spring-loaded pin, wherein the spring-loaded pin is released by a wearer from at least one locking hole when the pin release is triggered.

7. A grip device in accordance with claim 5, further comprising a levered pin release fastened to the spring-loaded pin, wherein the spring loaded pin is pulled out of at least one locking hole when the levered release is pressed.

8. A grip device in accordance with claim 5, wherein the drive and transmission further comprise:
   a friction planetary drive shaft coupled to the drive motor; and
   a friction planetary reduction connected to the friction planetary drive shaft.

9. A grip device in accordance with claim 8, further comprising a geared planetary reduction, contained within the backlock housing, and coupled to the backlock housing through a geared friction ring.

10. A grip device in accordance with claim 9, wherein the backlock further includes a backlock output gear which is coupled to the geared planetary reduction.

11. A grip device having at least two opposable digits and a drive unit, the drive unit comprising:
    (a) a drive motor mounted into the grip device;
    (b) a friction planetary drive shaft coupled to the drive motor;
    (c) a friction planetary reduction connected to the friction planetary drive shaft;
    (d) a backlock, mechanically coupled to the friction planetary reduction;
    (e) a backlock housing, containing the friction planetary reduction and backlock, having a plurality of locking holes formed into the housing; and
    (f) a spring loaded pin, configured to be releasably coupled into at least one locking hole in the backlock housing.

12. A grip device in accordance with claim 11, further comprising a geared planetary reduction, contained within the backlock housing and coupled to the backlock housing through a geared friction ring.

13. A grip device in accordance with claim 11, further comprising a pin release fastened to the spring-loaded pin, wherein the spring loaded pin is released from at least one locking hole when the pin release is triggered.

14. A grip device in accordance with claim 11, further comprising a levered pin release fastened to the spring-loaded pin, wherein the spring loaded pin is pulled out of at least one locking hole when the lever release is pressed.

15. A grip device in accordance with claim 11, further comprising
   (a) a backlock output gear connected to the backlock;
   (b) a two-speed transmission coupled to the backlock output gear, wherein the two-speed transmission provides greater speed under a reduced load and lower speed under an increased load.

16. A grip device in accordance with claim 14, further comprising:
   (a) an output gear reduction assembly connected to the two-speed transmission;
   (b) a sector gear, coupled to the output gear reduction assembly, configured to drive a digit of the prosthetic hand.

17. A grip device as in claim 16 wherein the output gear reduction assembly further comprises a three toothed gear, and wherein the sector gear is driven by the three toothed gear.

18. A prosthetic hand having at least two opposable digits and a drive linkage configured to move the opposable digits and provide a maintainable grip, the drive linkage comprising:
   (a) a drive motor mounted into the prosthetic hand;
   (b) a friction planetary drive and reduction coupled to the drive motor;
   (d) a backlock connected to the friction planetary drive and reduction;
   (e) a geared planetary reduction, contained within the backlock housing, and coupled to the backlock housing through a ring gear;
   (f) a backlock housing, containing the friction planetary reduction, backlock and geared planetary reduction, having a plurality of locking holes formed into the housing; and
   (g) a locking pin, releasably coupled into at least one locking hole in the backlock housing, wherein the backlock housing is free to move when the locking pin is removed which allows the grip maintained between the opposable digits to be immediately released.

19. A device in accordance with claim 18, wherein the releasing of the locking pin allows the backlock housing to move and thereby avoids the gear reduction ratios and backlock impedance contained in the backlock housing, allowing the reversal of the drive mechanism and the release of the grip between the opposable digits.

20. A device in accordance with claim 18, wherein the locking pin further comprises a spring-loaded shaft within the locking pin configured to lock into at least one locking hole.

21. A device in accordance with claim 18, wherein the locking pin further comprises a spring-loaded pin configured to lock into at least one locking hole.

* * * * *